United States Patent
McEwen et al.

(10) Patent No.: US 7,955,352 B2
(45) Date of Patent: Jun. 7, 2011

(54) SURGICAL TOURNIQUET CUFF FOR LIMITING USAGE TO IMPROVE SAFETY

(75) Inventors: James A. McEwen, Vancouver (CA); Michael Jameson, North Vancouver (CA)

(73) Assignee: Western Clinical Engineering, Ltd CA (US)

( * ) Notice: Subject to any disclaimer, the term of this patent is extended or adjusted under 35 U.S.C. 154(b) by 674 days.

(21) Appl. No.: 11/198,565

(22) Filed: Aug. 5, 2005

(65) Prior Publication Data
US 2007/0032818 A1 Feb. 8, 2007

(51) Int. Cl.
*A61B 17/00* (2006.01)
(52) U.S. Cl. .................................................. 606/202
(58) Field of Classification Search .......... 604/163, 604/171, 263; 606/202, 203; 340/10.1, 10.3
See application file for complete search history.

(56) References Cited

U.S. PATENT DOCUMENTS

| | | | |
|---|---|---|---|
| 3,670,735 A | 6/1972 | Hazlewood | |
| 3,892,229 A | 7/1975 | Taylor | |
| 4,013,069 A | 3/1977 | Hasty | |
| 4,326,416 A | 4/1982 | Fredberg | |
| 4,469,099 A * | 9/1984 | McEwen | 606/202 |
| 4,479,494 A * | 10/1984 | McEwen | 606/202 |
| 4,520,819 A | 6/1985 | Birmingham | |
| 4,605,010 A * | 8/1986 | McEwen | 600/499 |
| 4,635,635 A | 1/1987 | Robinette-Lehman | |
| 4,869,265 A | 9/1989 | McEwen | |
| 4,979,953 A | 12/1990 | Spence | |
| 5,193,549 A | 3/1993 | Bellin | |
| 5,201,758 A | 4/1993 | Glover | |
| 5,254,087 A | 10/1993 | McEwen | |
| 5,312,431 A | 5/1994 | McEwen | |
| 5,316,002 A | 5/1994 | Jackson | |
| 5,411,518 A | 5/1995 | Goldstein | |
| 5,413,582 A | 5/1995 | Eaton | |
| 5,439,477 A * | 8/1995 | McEwen | 606/203 |

(Continued)

FOREIGN PATENT DOCUMENTS
DE 4412832 A1 * 10/1994

OTHER PUBLICATIONS
U.S. Appl. No. 11/153,667, filed Jun. 15, 2005, Mcewen.

(Continued)

*Primary Examiner* — Darwin P Erezo
*Assistant Examiner* — Mark Mashack
(74) *Attorney, Agent, or Firm* — Hancock Hughey LLP (57) ABSTRACT

A surgical tourniquet cuff for limiting usage to improve safety, comprises: an inflatable portion having a length sufficient for encircling a patient's limb at a desired location; cuff connector means communicating pneumatically with the inflatable portion and adapted near an end for connecting to a tourniquet instrument to establish a releasable pneumatic connection; and a cuff usage register located at a predetermined distance from the end of the cuff connector means and adapted for containing a usage amount record indicative of an amount of a predetermined usage of the cuff. The cuff usage register may further contain a usage limit record indicative of a predetermined limit of the predetermined usage of the cuff. The cuff usage register may be further adapted for enabling the cuff usage record and the usage limit record to be read by a tourniquet instrument that is pneumatically connected to the inflatable portion through the cuff connector means.

12 Claims, 4 Drawing Sheets

U.S. PATENT DOCUMENTS

| | | | |
|---|---|---|---|
| 5,445,144 A | 8/1995 | Wodicka | |
| 5,454,831 A | 10/1995 | McEwen | |
| 5,556,415 A | 9/1996 | McEwen | |
| 5,575,762 A | 11/1996 | Peeler | |
| 5,578,055 A | 11/1996 | McEwen | |
| 5,584,853 A | 12/1996 | McEwen | |
| 5,607,447 A | 3/1997 | McEwen | |
| 5,649,954 A | 7/1997 | McEwen | |
| 5,681,339 A | 10/1997 | McEwen | |
| 5,733,304 A | 3/1998 | Spence | |
| 5,741,295 A | 4/1998 | McEwen | |
| 5,855,589 A | 1/1999 | McEwen | |
| 5,911,735 A * | 6/1999 | McEwen et al. | 606/201 |
| 5,931,853 A * | 8/1999 | McEwen et al. | 606/203 |
| 5,935,146 A | 8/1999 | McEwen | |
| 5,991,355 A * | 11/1999 | Dahlke | 377/15 |
| 6,605,103 B2 | 8/2003 | Hovanes | |
| 6,682,547 B2 * | 1/2004 | McEwen et al. | 606/202 |
| 6,884,255 B1 * | 4/2005 | Newton | 606/202 |
| 2003/0167070 A1 * | 9/2003 | McEwen et al. | 606/203 |
| 2004/0122419 A1 * | 6/2004 | Neuberger | 606/10 |
| 2004/0127937 A1 * | 7/2004 | Newton | 606/202 |
| 2005/0033351 A1 * | 2/2005 | Newton | 606/202 |
| 2005/0113815 A1 * | 5/2005 | Ritchie et al. | 606/15 |
| 2006/0287672 A1 * | 12/2006 | McEwen et al. | 606/202 |

OTHER PUBLICATIONS

U.S. Appl. No. 11/346,846, filed Feb. 3, 2006, McEwen.
U.S. Appl. No. 11/219,016, filed Sep. 1, 2005, McEwen.

* cited by examiner

SURGICAL TOURNIQUET CUFF FOR LIMITING USAGE TO IMPROVE SAFETY

FIELD OF THE INVENTION

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND OF THE INVENTION

A typical surgical tourniquet system of the prior art includes a tourniquet cuff for encircling a patient's limb at a desired location and a tourniquet instrument that includes flexible instrument tubing for connecting to the tourniquet cuff. The tourniquet cuff typically includes an inflatable portion, and the inflatable portion of the cuff is typically connected through a cuff port having a port connector to the instrument, thereby establishing a pneumatic passageway from the tourniquet instrument through the instrument tubing and the cuff port into the inflatable portion of the cuff.

Many types of surgical tourniquet systems, including tourniquet cuffs and tourniquet instruments, have been described in the prior art, such as those described by McEwen in U.S. Pat. No. 4,469,099, No. 4,479,494, No. 5,439,477 and by McEwen and Jameson in U.S. Pat. No. 5,556,415 and No. 5,855,589. Some prior-art tourniquet instruments include a pressure transducer to sense the pressure of gas at the instrument end of the pneumatic passageway and to enable the sensed pressure to be displayed for surgical staff. Many prior-art tourniquet instruments include a pressure regulator to increase and decrease the pressure of gas in the pneumatic passageway, and to maintain the pressure in the inflatable portion of the cuff near a reference pressure that is above a minimum pressure required to stop arterial blood flow past the cuff during a time period suitably long for the performance of a surgical procedure. Some tourniquet instruments of the prior art, as described for example by McEwen in U.S. Pat. No. 4,469,099, include audio-visual alarms to promptly alert users to any significant over-pressurization or under-pressurization of a connected tourniquet cuff away from a selected tourniquet reference pressure, and include audio-visual alarms to alert users to any excessive periods of pressurization of a connected cuff, because the surgical literature clearly shows that such conditions are hazardous and are associated with increased probabilities of tourniquet-related injuries to patients. A few tourniquet systems of the prior art, such as those described by McEwen in U.S. Pat. No. 4,479,494 and No. 5,439,477, include physiologic transducers to help automatically determine the minimum and safest tourniquet reference pressure required to stop arterial blood flow in the limbs of individual patients undergoing specific surgical procedures.

Tourniquet cuffs of the prior art can be grouped into three broad categories by their intended usage: (1) reusable tourniquet cuffs manufactured for usage outside the sterile surgical field in multiple surgical procedures, and for cleaning by users between successive procedures; (2) reusable tourniquet cuffs manufactured for usage within the sterile surgical field in multiple surgical procedures, and for cleaning and sterilization by specified sterilization processes between successive procedures; and (3) disposable tourniquet cuffs manufactured as sterile products suitable for usage within the sterile surgical field in one surgical procedure, and for disposal after the procedure.

Within each of these three broad usage categories, tourniquet cuffs of the prior art are supplied in a wide variety of sizes, shapes and designs matched to the intended surgical applications. Some of the largest tourniquet cuffs of the prior art are intended for use on patients having large, obese thighs with thigh circumferences of over 60 inches; such very large pneumatic cuffs typically require high tourniquet inflation pressures to stop arterial blood flow. In contrast, some of the smallest sizes of tourniquet cuffs are intended for the limbs of newborn infants, and typically require substantially lower tourniquet pressures to stop blood flow. This is an important consideration, because unnecessarily high tourniquet pressures have been shown to be associated with unnecessarily higher probabilities of injury to the patient. Some tourniquet cuffs of the prior art are designed to fit very snugly onto limbs having substantially cylindrical limb shapes at desired locations, while other cuffs are designed to fit limbs at locations that are substantially conical in shape. A close match between the limb shape and the shape of the tourniquet cuff has been shown in the surgical literature to substantially decrease the tourniquet pressure required to stop blood flow in a limb past an encircling cuff, and lower tourniquet pressures have been shown to be less hazardous for the patient.

Some designs of tourniquet cuffs of the prior art include two separate inflatable portions, often called dual bladders, for separately encircling a limb at proximal and distal locations to facilitate an anesthetic technique called Bier block anesthesia or intravenous regional anesthesia. A representative dual-bladder tourniquet cuff for Bier block anesthesia is described by McEwen in U.S. Pat. No. 5,312,431 and a representative prior-art tourniquet instrument for facilitating Bier block anesthesia is described by McEwen et al in U.S. Pat. No. 5,556,415. For Bier block anesthesia, a dual-bladder tourniquet cuff is used to perform two functions: to stop the flow of arterial blood into the limb, and to stop the outflow of an anesthetic liquid from the limb. For optimal safety in maintaining a bloodless surgical field and at the same time maintaining anesthesia in the limb, it is important that the selected cuff has a safe and appropriate size, shape and design, that the proximal and distal bladders encircling the limb are correctly identified, that the two sets of tubing from the tourniquet instrument are correctly connected to the matching proximal and distal bladders, and that the tourniquet pressure setting is appropriate for the identity and characteristics of the connected dual-bladder cuff. Any malfunction or failure of a dual-bladder tourniquet cuff during usage in Bier block anesthesia may be particularly hazardous because it may result in the sudden flow of a large bolus of anesthetic agent out of the limb and into systemic circulation, causing a possible loss of anesthesia and other anesthesia-related complications, as well as allowing a flow of arterial blood into the limb and surgical site, leading to possible blood loss and surgical complications.

Reusable tourniquet cuffs manufactured for usage outside the sterile surgical field in multiple surgical procedures, and for cleaning and disinfection by users between successive procedures, represent a common usage category of prior-art cuffs. All reusable cuffs will fail eventually, and cuff failure during surgery is hazardous for the patient. Some cuff failures may result in undetected blockages of the pneumatic passageway in the cuff, and may result in significant differences between the tourniquet pressure indicated by the instrument and the pressure actually applied by the cuff to the limb. Other cuff failures during surgery may be associated with a complete loss of cuff pressure onto the limb and may result in complications such as substantial blood loss, a sudden flow of arterial blood into the surgical site that may extend surgical time, complicate the surgical procedure and impair the quality of the surgical outcome. Also as noted above, failure of a cuff during Bier block anesthesia may additionally lead to the loss of anesthetic effect and anesthesia-related complications.

Reusable cuffs are subjected to a combination of usage conditions that will eventually result in cuff malfunction and failure, including: repeated cuff pressurization cycles, increasing cumulative periods of cuff inflation, high maximum inflation pressures, exposure to elevated temperatures, exposure to harmful cleaning or disinfection agents, natural ageing of cuff materials, and inadequate cuff maintenance and testing of functionality, materials, fasteners and connectors between uses. Any of those usage conditions may lead to cuff deterioration and failure, and the probability of such deterioration and failure increases with usage and time. In some hospitals and surgical centers, reusable tourniquet cuffs are cleaned, disinfected, visually examined and functionally tested by operating-room staff between successive usages, and tested and maintained more completely by biomedical engineering staff on a periodic basis, in accordance with established and written policies and procedures. However, this is not the case in many surgical settings. In those settings, reusable tourniquet cuffs may be cleaned or disinfected only occasionally, with various agents that may harm the cuff materials or functionality. Also in such settings, the quality of any visual examinations or functional tests of reusable tourniquet cuffs that may be performed from time to time is highly dependent on the knowledge, skill, training and vigilance of the individuals doing the tests and the time available for testing. Standardized criteria for determining whether a reusable tourniquet cuff is safe for continued usage have not yet been developed. As a result, in many settings a reusable tourniquet cuff of the prior art will continue in usage until substantial physical deterioration is obvious to experienced surgical staff and leads to its replacement, or until there is a suspected malfunction or complete failure of the reusable cuff during pre-surgical testing or during the surgical procedure itself.

Some reusable tourniquet cuffs of the prior art specifically allow sterilization by autoclaving, for use in sterile surgical fields. For example, the manufacturer of VBM reusable silicone tourniquet cuffs (VBM Medizintechnik GmbH, Robert-Bosch-Str. 7, D72172 Sulz a.N., Germany) provides autoclaving instructions and warnings. A typical process of autoclaving, or steam sterilization of a tourniquet cuff may involve the exposure of the cuff in a pressure vessel to saturated steam at an elevated temperature and pressure for several minutes to kill micro-organisms on the cuff. Although effective for sterilization, the elevated temperature, humidity and pressure of autoclaving can lead to degradation of cuff materials together with any residual cleaning and disinfecting agents on the materials, including softening, hydrolysis and changes in the physical and mechanical properties of the materials. As a result, some reusable and re-sterilizable cuffs known in the prior art have been formed of heat-resistant materials such as silicone and latex rubber. Some prior-art cuffs are accompanied by warnings that cuffs must be protected to reduce the likelihood of effects from high temperatures, humidity and pressure during autoclaving. For example, a change of cuff shape or a weakening of the retention strength of a cuff connector or a fastener from exposure of a cuff to a high temperature that persists after autoclaving could be hazardous in subsequent use. Some prior-art cuffs are supplied with a warning that the inflatable portions of the cuffs must be completely evacuated prior to autoclaving. Any rupture or weakening of the inflatable portions due to gas in the cuff during autoclaving could be hazardous in subsequent patient use. In general, suppliers of autoclavable cuffs of the prior art warn users that repeated autoclaving accelerates the natural ageing process of the cuff materials. All of the effects specified in such warnings for autoclavable cuffs serve to limit aspects of their safe usage, such as the number of inflation cycles, the cumulative inflation time, and the maximum inflation pressure before cuff failure. Any cuff failure during surgery may be hazardous for the patient, but no reusable autoclavable cuff known in the prior art includes means for limiting usage to improve safety.

Other tourniquet cuffs known in the prior art are supplied as sterile products and are intended for disposal after usage that is limited to one surgical procedure. As a result, the design characteristics of these disposable cuffs are intended to allow them to be applied and used safely and reliably within a sterile surgical field during one surgical procedure, and to be discarded cost-effectively after that procedure. For example, some disposable tourniquet cuffs of the prior art have a port that includes a very flexible thermoplastic tubing portion having a length sufficient to allow a user to easily bend the port away from the surgical site beyond the sterile surgical field for connection through a port connector to a tourniquet instrument. The various materials and components from which such prior-art disposable tourniquet cuffs are assembled are chosen to be sufficiently inexpensive to allow the cuff to be economically discarded after usage limited to a single surgical procedure, and also to be capable of sterilization by exposure to a specific sterilizing agent within a specific sterilizing process determined by the manufacturer, with no significant deterioration or change of properties that would impair the safety or performance of the cuffs after such sterilization.

Efforts have been made to reprocess and reuse tourniquet cuffs of the prior art that were originally supplied by their manufacturers as sterile products limited to a single use. Reprocessing efforts typically involve saving rather than discarding a disposable tourniquet cuff after surgery, visually examining the cuff to identify any obvious deterioration that might suggest reprocessing is not appropriate, attempting to remove any blood and other surgical debris by washing the cuffs with water combined with any of a variety of detergents or other cleaning liquids, disinfecting in some instances with various disinfecting agents, and in some cases conducting some functional tests of the cuff. Some of these prior-art disposable cuffs may be reused as non-sterile cuffs after only cleaning, or after only cleaning and disinfection, with no functional testing and with no attempt to re-sterilize the cuff. In other situations, cleaned cuffs may be re-packaged and then re-sterilized by exposure to a sterilization agent within a sterilization process that may be different from that determined by the original manufacturer to be safe and effective. Reprocessing of disposable tourniquet cuffs, with or without re-sterilization, may be carried out within hospitals or surgery centers or by third-party reprocessors, and the quality and methods of reprocessing are highly variable. Reprocessing of disposable tourniquet cuffs may result in hazards for the surgical patients on whom such cuffs are subsequently used. One such hazard arises from deterioration of cuff materials due to the use of any of a variety of chemical or physical agents that are attendant with the reprocessing, cleaning, disinfection and possible re-sterilizing processes. For example, exposure of a cuff to liquids during cleaning and disinfection may allow the liquids to enter and partially or completely block the pneumatic passageway within the port and inflatable portion of the cuff. If the cuff is re-sterilized as part of the reprocessing, any water remaining within the pneumatic passageway after cleaning may subsequently react chemically with ethylene oxide, a sterilizing agent commonly used in reprocessing, to form ethylene glycol, a sticky substance that may completely or partially block the pneumatic passageway. Repeated exposure of prior-art cuffs containing flexible thermoplastic materials to an elevated temperature during drying after cleaning or disinfection with liquids, or during re-sterilization, may soften thermoplastic materials and components, increasing the likelihood of hazardous deformation of some components, including: substantial deformation of the thermoplastic stiffener included in some prior-art cuffs that may impair the application of pressure by such a cuff to an underlying limb upon subsequent use in surgery; partial or complete blockages of the pneumatic passageways within ports or thermoplastic connectors of some prior-art cuffs; and weakening of the retention force of typical thermoplastic barb-type port connectors so that such connectors cannot establish or reliably maintain a gas-tight passageway between the tourniquet cuff and tourniquet instrument upon reuse. In general, repeated reuse of a disposable tourniquet cuff beyond the limit of usage specified by the manufacturer, including exposure to cleaning and disinfection agents and processes not anticipated by the manufacturer if reused as non-sterile cuffs, and including exposure to re-sterilization agents and processes if reused as sterile cuffs, may progressively increase the hazards for the surgical patients on whom the cuff is used.

In U.S. Pat. No. 6,682,547 McEwen et al. describe a tourniquet cuff having identification means indicative of a physical characteristic of the cuff and detectable by a connected tourniquet instrument. In U.S. Pat. App. Pub. US 20030167070 A1, McEwen et al. describe an adaptive tourniquet cuff system in which a tourniquet cuff carries identification means indicative of a physical characteristic of the cuff and in which a connected tourniquet instrument may automatically detect the physical characteristic of the cuff and adapt its operation in response to the detected physical characteristic. McEwen US 20030167070 A1 also describes the identification by a tourniquet instrument of prior exposure of a connected cuff to a potentially hazardous re-sterilization process. In pending U.S. patent application Ser. No. 11/153,667 McEwen et al. describe a disposable tourniquet cuff having means visually detectable by a user and automatically detectable by a connected tourniquet instrument to indicate exposure of the cuff to re-sterilization processes, indicating re-sterilization and possible reuse of a cuff originally manufactured and supplied as a sterile, single-use product. However, McEwen '547, McEwen US 20030167070 A1 and McEwen Ser. No. 11/153,667 do not describe means for limiting the usage of a specific tourniquet cuff so that its usage does not exceed a safe usage limit for that cuff, to improve safety. For example, the prior art does not describe apparatus for limiting the number of usages of a specific non-sterile, reusable tourniquet cuff so that usage of the cuff does not exceed a safe maximum number. Also, the prior art does not describe tourniquet apparatus for limiting the usage of reusable tourniquet cuffs manufactured as re-sterilizable cuffs to usage and re-sterilization within safe limits, including for example a limit of the cumulative inflation time, a limit of the maximum inflation pressure, a limit of the number of cycles of usage and re-sterilization, or a limit of the overall duration of usage from time of manufacture due to ageing of cuff materials. Further, the prior art does not describe apparatus for limiting the usage of a single-use tourniquet cuff to usage within safe usage limits, and to usage in only one surgical procedure, without relying on the detection of re-sterilization to indicate possible reuse, because some users may attempt to reuse single-use cuffs as non-sterile cuffs, without exposing them to re-sterilizing agents and re-sterilization processes between successive usages. There is a need for tourniquet cuff apparatus for limiting usage as described above to improve safety, and the present invention addresses that need.

DETAILED DESCRIPTION OF THE PREFERRED EMBODIMENT

Figure 1:
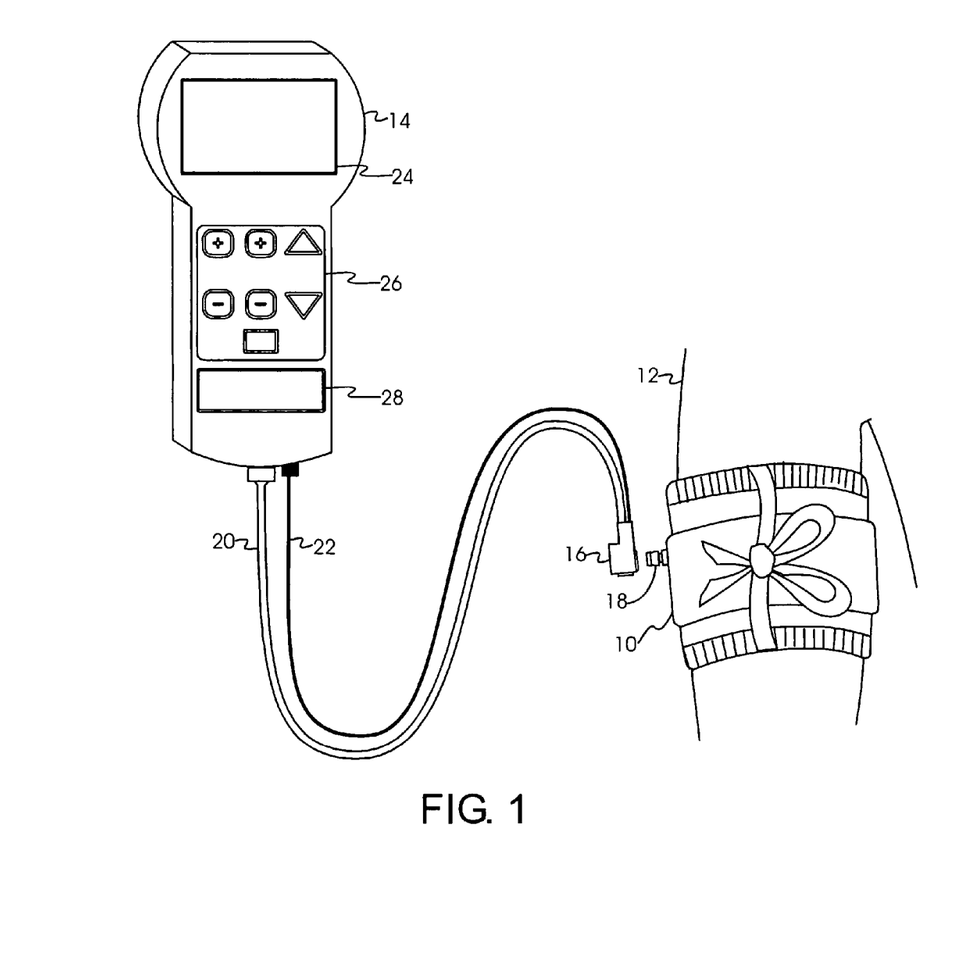
FIG. 1 is a pictorial representation of the preferred embodiment in a surgical application.

FIG. 1 is a pictorial representation of the preferred embodiment in a surgical application, showing tourniquet cuff 10 applied to patient limb 12 and pneumatically connectable to tourniquet instrument 14.

Tourniquet instrument connector 16 mates with cuff connector 18 on cuff 10 to form a releasable pneumatic connection to the inflatable portion of cuff 10. For clarity, in FIG. 1 tourniquet instrument connector 16 is shown disconnected from cuff connector 18 the pneumatic connection between instrument 14 and the inflatable portion of cuff 10 is formed when instrument connector 16 is mated with cuff connector 18. Instrument connector 16 is pneumatically connected to instrument 14 by flexible plastic tubing 20 and electrically connected to instrument 14 by multi-conductor cable 22.

Instrument 14 has a user interface consisting of pressure and time display panel 24, keypad 26 and cuff usage display panel 28. Pressure and time display panel 24 is employed for the selective display of any of the following alphanumeric information: actual cuff pressures as measured by instrument 14; reference or "set" cuff pressure levels, alarm reference "limits" or values; alphanumeric alarm messages describing detected alarm conditions and other information required for the operation of instrument 14.

Keypad 26 provides a means for a user of instrument 14 to control the operation of instrument 14. Keypad 26 includes an "inflate" key to initiate the inflation of cuff 10, a "deflate" key to initiate the deflation of cuff 10, and other keys to permit the user of instrument 14 to adjust the reference pressure level and set a time limit for an inflation time alarm.

When cuff 10 is pneumatically connected to tourniquet instrument 14, cuff usage display panel 28 is employed to indicate a record of the usage of cuff 10 and predetermined usage limits.

To improve patient safety by minimizing the risk of malfunction or failure of cuff 10 during a surgical procedure, the preferred embodiment maintains a record of cuff usage and inhibits further usage and alerts a surgical user if the amount of cuff usage has exceeded a predetermined limit.

Figure 3:
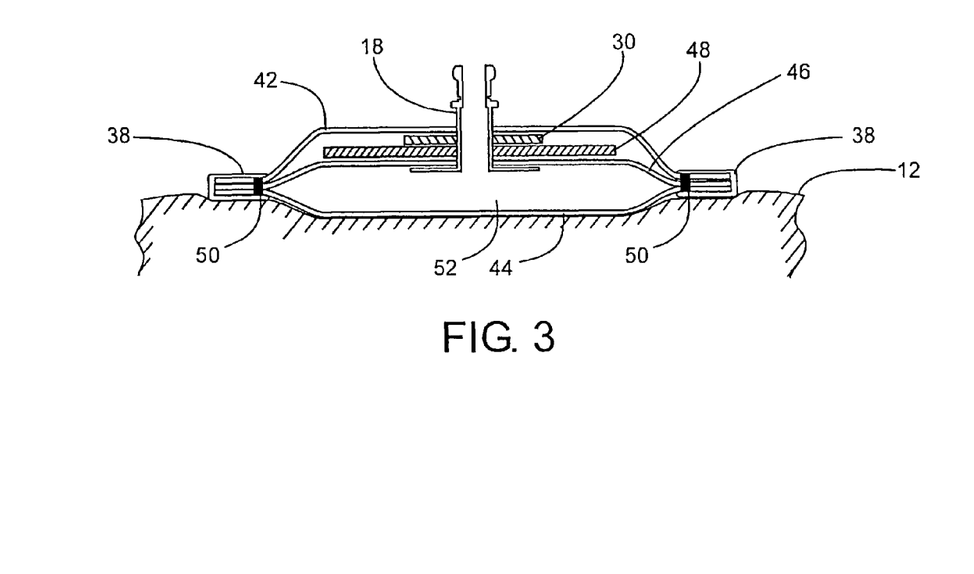
FIG. 3 is a section taken from FIG. 2, with the cuff applied to the patient's limb as shown in FIG. 1.
Figure 4:
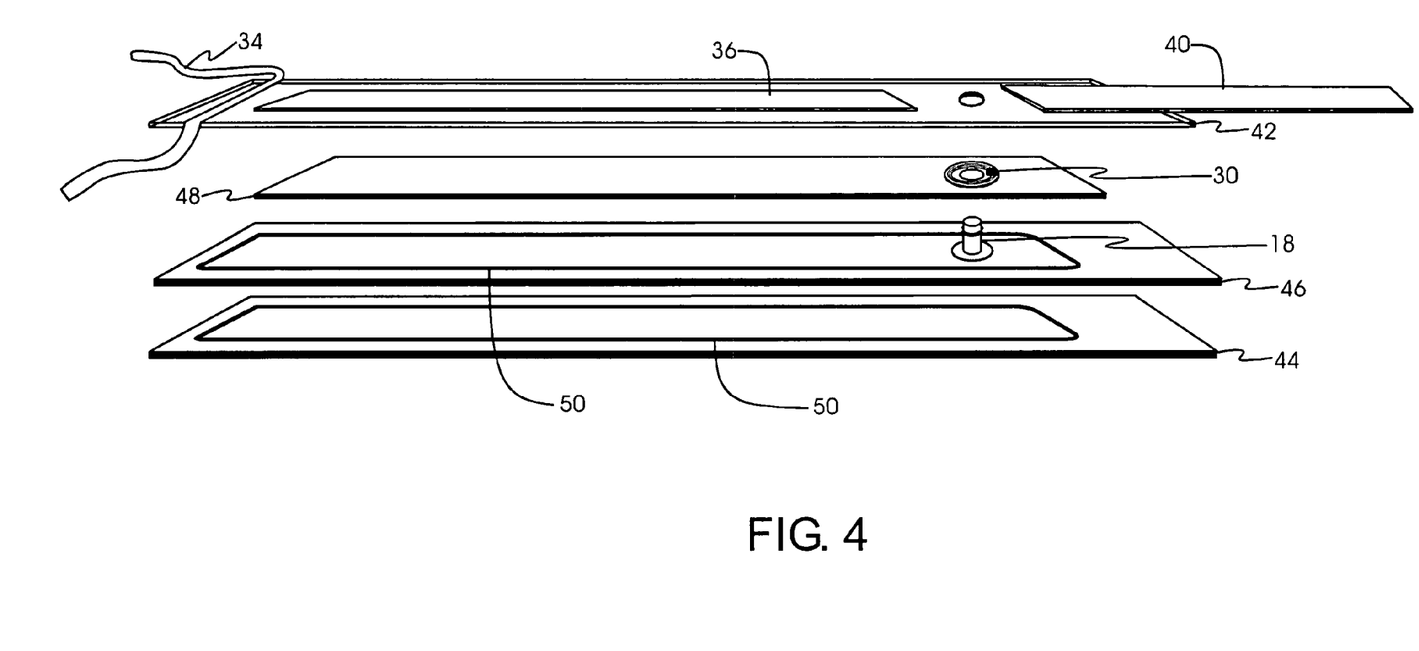
FIG. 4 is a section taken from FIG. 2, with the cuff applied to the patient's limb as shown in FIG. 1.

Integral to cuff 10 is a cuff usage register 30 shown in FIGS. 3 and 4. Cuff usage register 30 is located inside cuff 10 at a predetermined distance from the end of cuff connector 18. As described further below, cuff usage register 30 is used to maintain a record of usage of cuff 10 and predetermined usage limits.

In the preferred embodiment cuff usage register 30 is comprised of a radio frequency transponder with memory (RA-117-112A Texas Instruments, Dallas, Tex.). Physically, usage register 30 is 33 mm in diameter with an 18 mm diameter center hole and consists of a small integrated circuit bonded to a thin flexible polymer film substrate on which an aluminum foil antenna is patterned. The electronic circuits and antenna necessary for communication with usage register 30 are located within instrument connector 16 and comprise cuff usage register interface 32 which is shown in the block diagram in FIG. 5. Cuff usage register interface 32 within instrument connector 16 connects to instrument 14 via multi-conductor cable 22. The configuration of the electronic circuits and antenna comprising usage register interface 32 within instrument connector 16 limits communication with cuff usage register 30 to a distance of approximately 10 mm. This limited communication range, and the associated physical proximity and orientation of cuff usage register 30 to the end of cuff connector 18, helps assure that reliable and successful communication with cuff usage register 30 is limited to periods during which a gas-tight pneumatic connection to cuff connector 18 is established.

In the preferred embodiment cuff usage register 30 contains a detailed record of the usage of cuff 10 as well as predetermined usage limits. The usage limits and usage record include:

An Inflation Cycle Limit, defined to be a predetermined limit of the number of inflation cycles which cuff 10 may safely undergo. In the preferred embodiment an inflation cycle is the pressurization of cuff 10 to a level above an Inflation Cycle Pressure Limit for a period of time greater than a Inflation Cycle Time Limit before deflation to a pressure less than the Inflation Cycle Pressure Limit An Inflation Cycle Pressure Limit, defined to be a predetermined pressure limit used to specify the inflation cycle described above;

An Inflation Cycle Time Limit, defined to be a predetermined time limit that is used to specify the inflation cycle described above;

A Maximum Pressure Limit, defined to be a predetermined value representing the maximum pressure to which cuff 10 may be safely pressurized;

An Inflation Time Limit, defined to be a predetermined value representing the total duration of time during which cuff 10 may be safely pressurized;

An End of Usage Date, defined to be a predetermined value representing the calendar date after which date cuff 10 may no longer be safely used;

The Number of Cycles of Inflation, a value corresponding to the number of inflation cycles that cuff 10 has undergone;

The Maximum Pressure of Inflation, a value representing the maximum pressure to which cuff 10 has been pressurized;

The Cumulative Time of Inflation, a value representing the total amount of time that the cuff has been pressurized above a predetermined minimum pressure.

Usage register 30 may also contain a cuff identification record that uniquely identifies cuff 10 and may also indicate physical characteristics of cuff 10.

When instrument 14 is pneumatically connected to cuff 10, instrument 14 reads information from cuff usage register 30 and displays this information on cuff usage display 28. As described further below, instrument 14 also updates the information in usage register 30 based on the pressurization of cuff 10 while connected to instrument 14 and inhibits further pressurization of cuff 10 if the usage limits contained within cuff usage register 30 are exceeded.

Cuff Materials and Construction

As described below, cuff 10 is constructed of materials that are appropriate for a reusable tourniquet cuff manufactured for usage outside the sterile surgical field in multiple surgical procedures, and for cleaning by users between successive procedures. Cuff 10 is typically cleaned and disinfected between surgical procedures by clinicians using appropriate agents and methods that have been recommended by the manufacturer of cuff 10.

Figure 2:
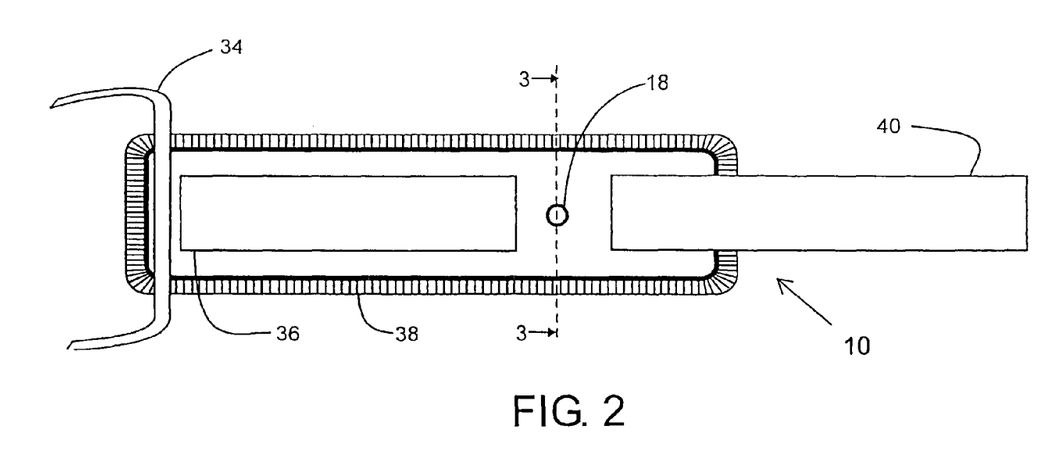
FIG. 2 shows the cuff portion of the preferred embodiment.

FIG. 2 shows cuff 10 of the preferred embodiment laid flat. Cuff 10 is similar in design and construction to the cuffs described by McEwen in U.S. Pat. No. 5,741,295, No. 5,649,954, No. 5,484,831 and by Robinette-Lehman in U.S. Pat. No. 4,635,635. In the preferred embodiment shown, cuff 10 is rectangular with a length sufficient to encircle an adult arm as shown in FIG. 1. Those skilled in the art will appreciate that the usage register described in the preferred embodiment may also be incorporated in cuffs of various sizes and shapes, such as those described by McEwen in U.S. Pat. No. 5,649,954. It will also be appreciated that a usage register may be integral to sterilizable reusable tourniquet cuffs manufactured for usage within the sterile surgical field in multiple surgical procedures in conjunction with cleaning and sterilization by specified sterilization processes between successive procedures; and to disposable tourniquet cuffs manufactured as sterile products suitable for usage within the sterile surgical field in one surgical procedure and for disposal after the procedure.

In addition to usage register 30, cuff 10 comprises cuff connector 18, tie ribbon 34, loop material 36, edge trim 38, and hook material 40.

In use, cuff 10 is wrapped snugly around limb 12 (see FIG. 1) and secured circumferentially around the limb when the user engages hook material 40 to loop material 36. Tie ribbon 34 is a soft fabric ribbon material (Grosgrain ⅝" wide, Dynatex Textiles Inc., Toronto, Ontario, Canada) and allows the user to pull cuff 10 snug around the limb. When cuff 10 is in position and secured circumferentially around the limb, the user ties tie ribbon 34 as shown in FIG. 1 to help prevent the cuff from sliding proximally or distally on the limb when inflated. Edge trim 38 is made of similar material to tie ribbon 34 and helps prevent chafing of the patient's limb by the edges of cuff 10.

FIG. 3 is a section 3 taken from FIG. 2, with cuff 10 applied to limb 12 (as shown in FIG. 1) and cuff 10 inflated. FIG. 4 is an exploded view of the layers that comprise cuff 10. Referring first to FIG. 3, top layer 42 and bottom layer 44 are made of woven nylon cloth coated with thermoplastic material (for example, 70 Denier brushed nylon cloth coated on one surface with thermoplastic polyurethane 0.006" thick) on the surface facing middle layer 46. Middle layer 46 is made of nylon cloth coated with thermoplastic material on both sides (for example, 200 Denier nylon cloth coated on both sides with thermoplastic polyurethane 0.006" thick). Stiffener 48 is made of plastic sheet having greater stiffness than layers 42, 44, and 46 but flexible enough to be wrapped around the limb (for example 0.020" thick polyethylene sheet), and cut to a rectangular shape fitting within the perimeter of cuff 10.

Cuff usage register 30 is adhesively bonded to stiffener 48 concentric to the location where cuff connector 18 passes through stiffener 48. This configuration insures correct orientation and location for reliable communication with usage register interface 32 when instrument connector 16 is mated with cuff connector 18.

Top layer 42, middle layer 46, and bottom layer 44 are joined around a continuous perimeter within the perimeter of cuff 10 at bladder seal 50, thereby forming inflatable bladder 52 between middle layer 46 and bottom layer 44 and enclosing thermoplastic stiffener 48 and cuff usage register 30 between top layer 42 and middle layer 46. When secured circumferentially around the limb as shown in FIG. 1, stiffener 48 helps direct the expansion of inflatable bladder 52 radially inwards towards the limb upon inflation of the cuff to more uniformly distribute pressure onto limb 12.

Bladder seal 50 is formed by a heat and pressure joining process, typically radio-frequency welding using a selected sealing die. The heat of the joining process is selected to temporarily melt a portion of the thermoplastic materials in layers 42, 44, and 46, causing them to fuse together in the area of bladder seal 50.

Cuff connector 18 is molded from thermoplastic and has a flange which is bonded to middle layer 46 to form pneumatic passageway extending into inflatable bladder 52. The flange surface of cuff connector 18 is permanently joined to middle layer 46 by a heat sealing process similar to that used to form bladder seal 50 (as described above). The physical shape and outer surface of cuff connector 18 is adapted to form a gas tight pneumatic passageway when mated with instrument connector 16.

FIG. 4 is an exploded view of the material layers that comprise cuff 10. Cuff usage register 30 is shown positioned on stiffener 48 such that cuff connector 18 passes through cuff usage register 30 thereby ensuring cuff usage register 30 maintains its position in proximity to cuff connector 18.

Cuff 10 has an outer surface defined by the outer surfaces of top layer 42, bottom layer 44 and cuff connector 18. Cuff usage register 30 is enclosed within the outer surface of cuff 10 at predetermined position and orientation adapted to permit short range wireless communication with usage register interface 32 when cuff connector 16 is mated with cuff connector 18. Enclosing usage register 30 within the outer surface of cuff 10 provides protection for cuff usage register 30 from damage that may occur during the use and cleaning of cuff 10. Cuff usage register 30 cannot be removed from cuff 10 or tampered with without causing obvious physical damage to the outer surface of cuff 10.

It will be apparent that cuff 10 may adapted for use in a sterile surgical field by the addition of flexible plastic tubing between inflatable bladder 52 and an appropriately adapted cuff connector 18 so as to permit connection to instrument 14 outside of the sterile surgical field. It will also be apparent that other components could be selected to form cuff register 30 and that cuff register 30 could be enclosed within the outer surface of cuff 10 by being embedded within connector 18 such that cuff register 30 retains the correct orientation and distance from the end of cuff connector 18 to permit communication with usage register interface 32 when instrument connector 16 is mated with cuff connector 18 to establish a gas-tight pneumatic passageway.

Instrument Hardware

Figure 5:
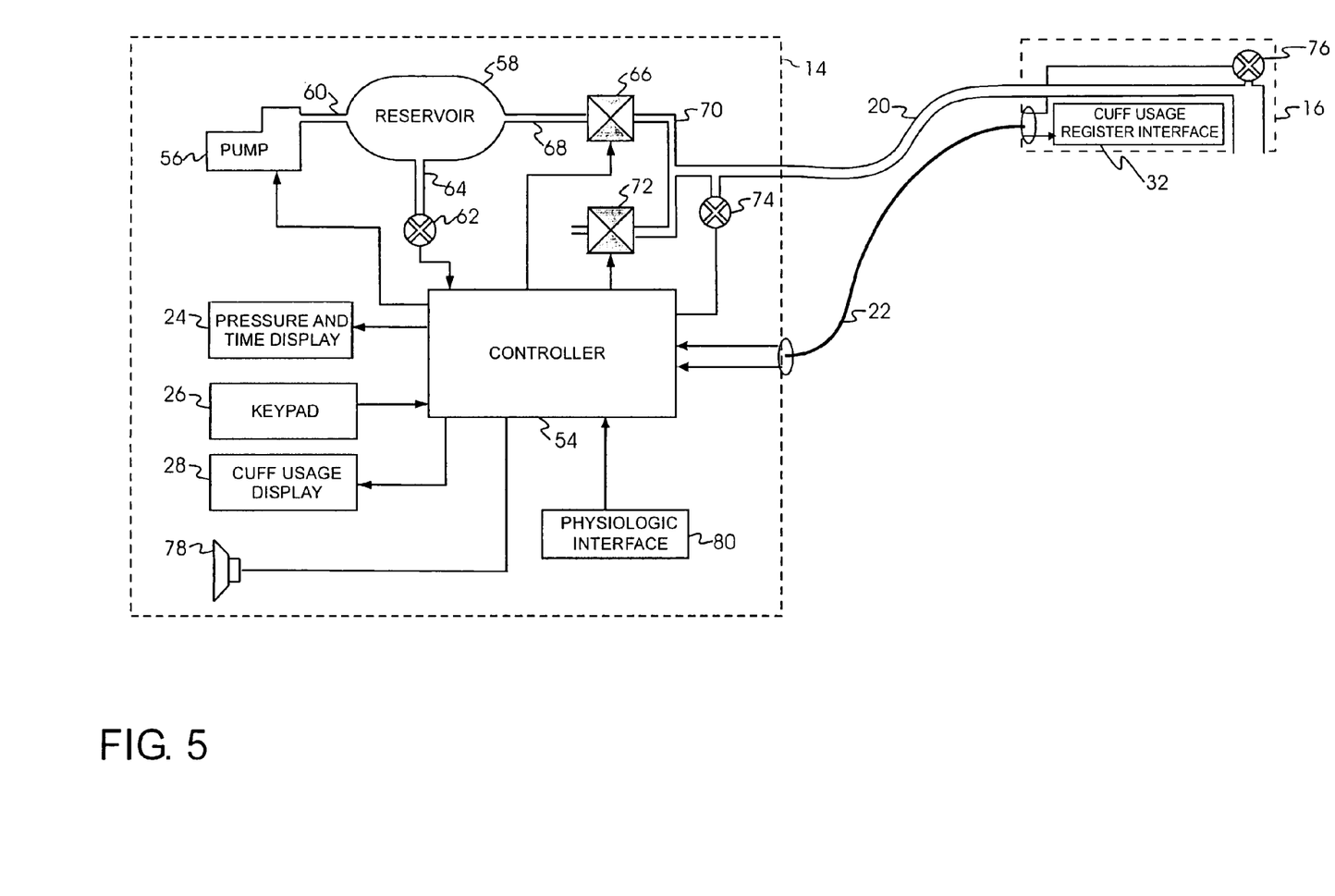
FIG. 5 is a block diagram of the preferred embodiment.

Referring to the block diagram of instrument 14 shown in FIG. 5, controller 54 comprises a microcontroller (ATMEGA128, Atmel Corp., San Jose, Calif.), associated memory and control software, analog and digital peripheral interface circuitry, timers, real time clock and other necessary support components.

As shown in FIG. 5, pneumatic pump 56 is pneumatically connected to reservoir 58 by tubing 60. In response to control signals from controller 54, pump 56 operates to pressurize reservoir 58. Reservoir pressure transducer 62 is pneumatically connected by tubing 64 to reservoir 58 and generates a reservoir pressure signal. The reservoir pressure signal is communicated to controller 54. Controller 54 acts to maintain the pressure in reservoir 58 near a reservoir pressure level, typically 100 mmHg greater than the cuff reference pressure level. Controller 54 in response to the reservoir pressure level and the reservoir pressure signal activates pump 56 to maintain the level of the reservoir pressure signal near the reservoir pressure level.

Inflation valve 66 (EVO-3-12V, Clippard Instrument Laboratory, Cincinnati, Ohio) is configured as a two position normally closed valve. One side of the valve is pneumatically connected via tubing 68 to reservoir 58 the other side of the valve is connected to bladder 52 within cuff 10 via the pneumatic passageway formed by manifold 70, tubing 20, instrument connector 16 and cuff connector 18. When energized by controller 54, inflation valve 66 moves to the open position and allows pressurized gas to flow from reservoir 58 to cuff 10, thereby increasing the pressure of gas in the inflatable bladder 52 of cuff 10.

Deflation valve 72 (EVO-3-12V, Clippard Instrument Laboratory, Cincinnati, Ohio) is configured as a two position normally closed valve. One side of the valve is pneumatically connected to cuff 10 via the pneumatic passageway formed by manifold 70, tubing 20, instrument connector 16 and cuff connector 18, the other side is open to atmosphere. When energized by controller 54, deflation valve 72 moves to the open position and allows pressurized gas to flow from cuff 10 to atmosphere, thereby decreasing the pressure of gas in inflatable bladder 52 within cuff 10.

Manifold pressure transducer 74 is pneumatically connected to manifold 70 and generates a manifold pressure signal representative of the pressure within manifold 70 which is communicated to controller 54.

As shown in FIG. 5 cuff pressure transducer 76 is located within instrument connector 16 and communicates pneumatically with the gas passageway within instrument connector 16 and thereby directly with inflatable bladder 52 when cuff connector 18 is mated with instrument connector 16. Cuff pressure transducer 76 generates a cuff pressure signal representative of the pressure within cuff 10 which is communicated to controller 54 via multi-conductor cable 22.

The direct pneumatic connection between inflatable bladder 52 of cuff 10 and cuff pressure transducer 76 provides for an accurate indication of the actual pressure of gas within cuff 10 at any time. Pressure transducer 76 will continue to accurately indicate the pressure of gas within cuff 10 even if tubing 20 should become occluded during use.

It will be apparent that transducer 76 could be located within cuff 10 to be in direct communication with inflatable bladder 52 and coupled to controller 54 via the same or similar wireless interface employed between usage register interface 32 and cuff usage register 30.

As noted above, controller 54 will, in response to generated alarm signals alert the user of an alarm condition by the display of appropriate alarm messages on pressure and time display 24 and by producing audible tones. Speaker 78 is connected to controller 54, and electrical signals having different frequencies to specify different alarm signals and conditions are produced by controller 54 and converted to audible sound by loud speaker 78.

Physiologic interface 80 provides a means for controller 54 to interface with and receive information from physiologic sensors. Controller 54 may if desired, automatically adjust the cuff pressure reference level in response information received from physiologic sensors via physiologic sensor interface 80. For example, the cuff pressure reference level may be automatically adjusted by controller 54 in response to a sensor for determining the minimum effective cuff pressure within cuff 10 required for occluding blood flow past cuff 10. Also, controller 54 may automatically adjust the cuff pressure reference level in response to changes in venous pressure which may occur during intravenous regional anesthesia, and in response to changes in other physiologic parameters such as blood pressure.

Pressure Regulation

A user of instrument 14 may use keypad 26 to select a reference pressure level; this is the pressure of gas that instrument 14 will attempt to maintain in the inflatable portion of cuff 10 when cuff 10 is inflated. Controller 54 will generate high or low pressure alarm signals if the pressure in cuff 10 cannot be maintained near the selected reference pressure level. If the cuff pressure level exceeds the reference pressure level by 15 mmHg a high pressure alarm signal will be generated by controller 54. If the cuff pressure level falls below the reference pressure level by 15 mmHg a low pressure alarm signal will be generated by controller 54.

When instrument connector 16 is mated with cuff connector 18 and controller 54 detects that the "inflate" key on keypad 26 has been depressed by a user of instrument 14, controller 54 first tests, as described further below, to ensure the usage limit for cuff 10 has not been exceeded. If the cuff usage limit has been exceeded the user is alerted by messages displayed on display panels 24 and 28 and by audio tones, and controller 54 does not proceed to inflate cuff 10. If the usage limit for cuff 10 has not been exceeded, controller 54 operates to inflate cuff 10 to a pressure near the selected reference pressure level and to then regulate the pressure in cuff 10 near the reference pressure level until such time that controller 54 detects that the "deflate" key on keypad 26 has been depressed by a user of instrument 14. Controller 54 may also inflate, adjust the reference pressure level, and deflate cuff 10 automatically in response to signals from physiologic interface 80.

To inflate and regulate the pressure in cuff 10 controller 54 includes a pressure regulator; the pressure regulator in the preferred embodiment is implemented as a control algorithm that operates as described below. At regular predetermined regulation intervals of 40 ms controller 54 computes a pressure error signal. The pressure error signal corresponds to the difference between the reference pressure level and the cuff pressure level. Controller 54 uses the pressure error signal as a term in a proportional integral control algorithm to calculate activation time intervals for inflation valve 66 and deflation valve 72. To increase the gas pressure in cuff 10 when the cuff pressure signal is below the reference pressure level, the activation time interval for deflation valve 72 is set to zero and the activation time interval for inflation valve 66 is proportional to the magnitude of the pressure error signal and the integral of the pressure error signal. To decrease the gas pressure in cuff 10 when the cuff pressure signal is above the reference pressure level, the activation time interval for inflation valve 66 is set to zero and the activation time interval for deflation valve 72 is proportional to the magnitude of the pressure error signal and the integral of the pressure error signal. Controller 54 limits the maximum valve activation time intervals of valve 66 and valve 72 to the regulation interval time (40 ms). It will be appreciated by those skilled in the art that alternate pressure regulation algorithms could be employed to control the activation of inflation valve 66 and deflation valve 72 in response to a cuff pressure signal and a reference pressure level, or that proportional valves could be used instead of the valves used in the preferred embodiment.

In order to correctly regulate the pressure of gas in cuff 10 at a pressure near the cuff pressure reverence level and correctly indicate over and under pressure alarm conditions, controller 54 must have available an accurate indication of the pressure within the inflatable portion of cuff 10. In the preferred embodiment the accurate measurement of the pressure of gas in cuff 10 is facilitated by cuff pressure transducer 76 and the direct pneumatic connection between the inflatable portion of cuff 10 and transducer 76. The connection between the inflatable portion of cuff 10 and transducer 76 is made within instrument connector 16.

While regulating the pressure within cuff 10, controller 54 compares the level of the manifold pressure signal with the level of the cuff pressure signal. If the level of the manifold pressure level differs substantially from the cuff pressure signal controller 54 acts to alert the user that an occlusion of tubing 20 may have occurred or other fault condition.

Cuff Usage Register

Referring again to the block diagram in FIG. 5, controller 54 communicates with cuff usage display 28 to display information obtained from cuff usage register 30 which is integral to cuff 10.

To read and write information to cuff usage register 30 controller 54 sends commands and data to cuff usage register interface 32 located in instrument connector 16. Usage register interface 32 communicates with controller 54 via multi-conductor cable 22. Usage register interface 32 responds to commands from controller 54 to detect the presence of usage register 30, to read values from usage register 30, and to write values to usage register 30.

Controller 54 polls usage register interface 32 to detect the presence of usage register 30. When instrument connector 16 is mated with cuff connector 18 to establish a pneumatic passageway, thus allowing usage register interface 32 to establish communication with cuff usage register 30, usage register interface 32 communicates to controller 54 that usage register 30 has been detected and values may now be read from and written to usage register 30. When instrument connector 16 is not connected to cuff connector 18 and the presence of usage register 30 is not detected by controller 54, controller 54 acts to inhibit activation of the pressure regulator described above and to display a message on cuff usage display 28 to indicate that a pneumatic connection has not been established to cuff 10.

Cuff usage register 30 contains non-volatile electrically alterable memory. Values representing amounts and limits of cuff usage may be both written to and read from selected memory locations within cuff usage register 30. Selected memory locations may also be configured as read only which inhibits the further writing and updating of values in these locations. Memory locations may be written to and then configured as read only at the time cuff 10 is manufactured.

Memory locations containing values representing usage limits are written with predetermined values at the time cuff 10 is manufactured and then configured as read only locations to prevent any subsequent modification of the limits. Usage limits are chosen at the time of manufacture to ensure continued safe operation of cuff 10 within the confines of the construction methods and physical materials used in the manufacture of cuff 10.

Memory locations containing values representing a record of cuff usage are configured as read/write so that they may be updated by controller 54 via usage register interface 32 when cuff 10 is pressurized.

As defined above, in the preferred embodiment the usage limits stored in usage register 30 are as follows: Inflation Cycle Limit; Inflation Cycle Pressure Limit; Inflation Cycle Time Limit; Maximum Pressure Limit; Inflation Time Limit; and End of Usage Date. Also, as defined above the usage record stored in usage register 30 includes the following: Number of Cycles of Inflation; Maximum Pressure of Inflation; and Cumulative Time of Inflation.

Other memory locations may be used to store values to uniquely identify cuff 10 and to represent information regarding the physical characteristics of cuff 10 such as: cuff length, the cuff type, the cuff shape, and recommended cuff pressures. For example, instrument 14 may be configured with two independent pressure regulators, associated pneumatics and usage register interfaces to permit it to independently pressurize two cuff bladders such as is required for a dual-bladder tourniquet cuff used for Bier block anesthesia. Cuff and bladder identification information stored in the usage register for each cuff bladder can be used by instrument 14 to alert the operator that the cuff is correctly identified, that the two sets of tubing and connectors from the tourniquet instrument are correctly connected to the matching proximal and distal bladders, and that the tourniquet pressure setting is appropriate for the identity and characteristics of the connected dual-bladder cuff.

In the preferred embodiment usage limits are established and set at the time of cuff manufacture and usage records are modified only by tourniquet instrument 14. It will be apparent that various security methods known in the art could be used to prevent unauthorized modification of the contents of usage register 30 by instruments other than tourniquet instrument 14.

When instrument connector 16 is mated with cuff connector 18 and controller 54 confirms that usage register 30 has been detected and that values may be read from and written to usage register 30, controller 54 reads and stores in its internal memory the usage limits and usage record from usage register 30, via usage register interface 32. Controller 54 then displays these values on cuff usage display 28.

Controller 54 next compares the usage record to the usage limits as follows: The Number of Cycles of Inflation is compared with the Inflation Cycle Limit, if the Number of Cycles of Inflation is equal to or greater than the Inflation Cycle Limit a warning message is displayed on cuff usage display 28 and the inflation of cuff 10 is inhibited; the Maximum Pressure of Inflation is compared with the Maximum Pressure Limit, if the Maximum Pressure of Inflation is greater than the Maximum Pressure Limit a warning message is displayed and the inflation of cuff 10 is inhibited; the Cumulative Time of Inflation is compared with the Inflation Time Limit, if the Cumulative Time of Inflation is greater than the Inflation Time Limit a warning message is displayed and the inflation of cuff 10 is inhibited; the End of Usage Date is compared with the current date and if the current date is greater than the End of Usage Date a warning message is displayed on cuff usage display 28 and the inflation of cuff 10 is inhibited.

In addition, controller 54 acts to limit the maximum cuff reference pressure selectable by a user of instrument 14 to the Maximum Pressure Limit for cuff 10 retrieved from cuff usage register 30. This prevents an operator from selecting pressure levels that are potentially damaging to cuff 10.

If controller 54 does not detect that any usage limit for cuff 10 has been exceeded, controller 54 proceeds, as described above, to pressurize cuff 10 when a user of instrument 14 activates the "inflate" key on keypad 26.

In the preferred embodiment, controller 54 inhibits inflation of cuff 10 if the usage limit has been exceeded. It will be apparent that controller 54 could be configured to allow inflation of cuff 10 when a usage limit has been exceeded by requiring the operator to use keypad 26 to acknowledge that the usage limit for cuff 10 has been exceeded before inflating cuff 10.

To update the Number of Cycles of Inflation controller 54 operates as follows. Controller 54 monitors the cuff pressure level as indicated by cuff pressure transducer 76. When the cuff pressure level exceeds the Inflation Cycle Pressure Limit retrieved from cuff usage register 30, controller 54 starts a timer, this timer continues to run while the cuff pressure level remains above the Inflation Cycle Pressure Limit and measures the duration of time that the pressure level exceeds the limit. When the cuff pressure level does not exceed the Inflation Cycle Pressure Limit, controller 54 stops and resets this timer. When the time indicated by the timer exceeds the Inflation Cycle Time Limit, controller 54 increments the Number of Cycles of Inflation by 1 and writes via usage register interface 32 the updated value to usage register 30.

In the preferred embodiment the Inflation Cycle Pressure Limit and the Inflation Cycle Time Limit are used to define what level and duration of pressurization of cuff 10 is considered to be an Inflation Cycle. These limits can be selected so as to permit the functional testing of cuff 10 using appropriate test methods by operating-room staff between successive usages, and the testing by biomedical engineering staff on a periodic basis, without such testing affecting the available Number of Cycles of Inflation of the cuff.

To update the Maximum Pressure of Inflation controller 54 monitors the cuff pressure level as indicated by cuff pressure transducer 76. If at any time the cuff pressure level exceeds the Maximum Pressure of Inflation, controller 54 sets the Maximum Pressure of Inflation to the cuff pressure level and writes via usage register interface 32 the updated value to usage register 30. This ensures that the usage record for cuff 10 reflects the peak pressure to which cuff 10 has been exposed. Controller 54 also compares the cuff pressure level to the Maximum Pressure Limit and alerts the operator by displaying an alarm message and activating an audio tone if the cuff pressure level exceeds the Maximum Pressure Limit.

In the preferred embodiment the Cumulative Time of Inflation is measured in minutes. To update the Cumulative Time of Inflation controller 54 increments the Cumulative Time of Inflation and writes the updated value to usage register 30 each minute that the cuff pressure level remains above a predetermined minimum pressure level. In the preferred embodiment the predetermined minimum pressure level is the same as the Inflation Cycle Pressure Limit used to determine usage cycles. It will be apparent that alternate pressure limits could be used and the limit predetermined by controller 54 or recorded as a separate limit in cuff usage register 32.

Examples of Typical Use

To enable a better understanding of the preferred embodiment and the function of the cuff usage record and limits, examples of the preferred embodiment's typical use in surgical procedures are described below.

In this first example cuff 10 is a reusable tourniquet cuff that may be cleaned and disinfected prior to each application to a patient by appropriate methods. The manufacturer has performed testing and determined usage limits for the cuff that will permit cuff 10 to be used safely under normal conditions. The usage limits stored in cuff usage register 30 are: Inflation Cycle Limit 10; Inflation Cycle Pressure Limit 50 mmHg; Inflation Cycle Time Limit 10 minutes; Maximum Pressure Limit 500 mmHg; Inflation Time Limit 1200 minutes.

Cuff 10 is selected for application to a patient for use during a surgical procedure and connected to instrument 14. Instrument 14 then reads and displays the usage limits above and the usage record of cuff 10. The usage record from cuff 10 shows the following usage: Number of Cycles of Inflation 7; Maximum Pressure of Inflation 300 mmHg, Cumulative Time of Inflation 600 minutes.

As none of the usage limits have been exceeded instrument 14 will permit cuff 10 to be pressurized when the user activates the "inflate" key on keypad 26.

In this example, the operator wishes to first test cuff 10 by pressurizing it to 400 mmHg prior to applying it to the patient for the surgical procedure. To test cuff 10 the operator selects a reference pressure of 400 mmHg and inflates cuff 10, after 3 minutes the operator deflates cuff 10 by activating the deflate key on keypad 26. During the test instrument 14 updates usage record maintained in cuff usage register 30, the usage record for cuff 10 now shows the following: Number of Cycles of Inflation 7; Maximum Pressure of Inflation 400 mmHg, Cumulative Time of Inflation 603 minutes. Note that the Number of Cycles of Inflation has not increased because the Inflation Cycle Time Limit of 10 minutes was not exceeded during the testing however, the maximum pressure of inflation and cumulative inflation time have both increased.

The operator next applies cuff 10 to the patient and selects a cuff reference pressure of 300 mmHg. Cuff 10 is inflated for a total of 60 minutes during the surgical procedure. At the end of the surgical procedure cuff usage register 30 contains the following record of cuff usage: Number of Cycles of Inflation 8; Maximum Pressure of Inflation 400 mmHg, Cumulative Time of Inflation 663 minutes. Note that the Number of Cycles of Inflation has increased by 1 and Cumulative Time of Inflation has increased by 60 minutes.

In this example cuff 10 has 2 remaining inflation cycles that it can be subjected to in subsequent surgical procedures before instrument 14 inhibits further pressurization of cuff 10.

Another example of the preferred embodiment's typical use in surgical procedures is as follows. In this example cuff 10 is a low cost disposable tourniquet cuff which is sterilized by the manufacturer and supplied in a sterile state to the user. Due to the materials and methods used in the manufacture of this cuff the usage limits stored in cuff usage register 30 are predetermined by the manufacturer to be: Inflation Cycle Limit 1; Inflation Cycle Pressure Limit 50 mmHg; Inflation Cycle Time Limit 10 minutes; Maximum Pressure Limit 400 mmHg; Inflation Time Limit 240 minutes.

Cuff 10 is selected for application to a patient for use during a surgical procedure and connected to instrument 14. Instrument 14 then reads and displays the usage limits above and the usage record of cuff 10. The usage record from cuff 10 shows the following usage: Number of Cycles of Inflation 0; Maximum Pressure of Inflation 0 mmHg, Cumulative Time of Inflation 0 minutes. Because cuff 10 has not been previously used the usage record shows 0 values.

The operator next applies cuff 10 to the patient and selects a cuff reference pressure of 250 mmHg. As none of the usage limits have been exceeded instrument 14 will permit cuff 10 to be pressurized when the user activates the "inflate" key on keypad 26. Cuff 10 is inflated for a total of 80 minutes during the surgical procedure. At the end of the surgical procedure cuff usage register 30 contains the following record of cuff usage: Number of Cycles of Inflation 1; Maximum Pressure of Inflation 250 mmHg, Cumulative Time of Inflation 80 minutes.

In this example the Number of Cycles of Inflation now equals the Inflation Limit stored in usage register 30 in cuff 10. If cuff 10 is subsequently connected to instrument 14, instrument 14 will detect that the usage limit for this cuff has been exceeded and alert the operator and inhibit pressurization of cuff 10. This prevents cuff 10 from being used beyond the usage limits set by the manufacturer for the safe and effective use of cuff 10.

The embodiment illustrated is not intended to be exhaustive or limit the invention to the precise form disclosed. It is chosen and described in order to explain the principles of the invention and its application and practical use, and thereby enable others skilled in the art to utilize the invention.

We claim:

1. A tourniquet cuff apparatus for limiting usage to improve safety, comprising
    an inflatable portion having a length sufficient for encircling a patient's limb at a desired location, and a stiffener member enclosed therein;
    a tubular cuff connector attached to the inflatable portion and communicating pneumatically with the inflatable portion and adapted near an outer end thereof for connecting to a tourniquet instrument to establish a releasable pneumatic connection; and
    a wireless cuff usage register connected to and in contact with the stiffener member and located adjacent to the cuff connector at a predetermined distance from the end of the cuff connector and adapted for containing a usage amount record indicative of an amount of usage of the cuff.

2. The apparatus as described in claim 1 wherein the cuff usage register is adhesively bonded to the stiffener member and further contains a usage limit record indicative of a predetermined limit of usage of the cuff.

3. The tourniquet cuff apparatus as described in claim 1 further comprising a tourniquet instrument connector with incorporated interface for reading the wireless cuff usage register, wherein the cuff usage register is further adapted for enabling the cuff usage record and the usage limit record to be read by the tourniquet instrument connector interface when that tourniquet instrument connector is pneumatically connected to the cuff connector.

4. The apparatus as described in claim 3 wherein the tourniquet instrument connector interface has a range limited to substantially the distance between the stiffener member and the outer end of the tubular cuff connector.

5. The apparatus as described in claim 4 wherein the range is about 10 millimeters.

6. The apparatus as described in claim 2 wherein the wireless cuff usage register is oriented to surround the inner end of the tubular cuff connector and the predetermined limit of usage is the maximum pressure of inflation.

7. The apparatus as described in claim 2 and including a tourniquet instrument having means for reading the usage amount record and the usage limit record while the pneumatic connection is established and for producing a usage alert signal if the amount indicated by the usage amount record is not less than the predetermined limit indicated by the usage limit record.

8. The apparatus as described in claim 1 and including a tourniquet instrument adapted for reading an initial usage amount record indicative of an initial amount of cuff usage upon establishment of the pneumatic connection, for calculating an incremental amount of the cuff usage while the cuff is connected to the tourniquet instrument, and for writing a cumulative usage amount record into the cuff usage register that is indicative of the sum of the initial amount and the incremental amount.

9. The apparatus as described in claim 2 wherein the predetermined limit of cuff usage is the maximum pressure of inflation and including a tourniquet instrument adapted for reading the usage amount record indicative of a first amount of cuff usage upon connection to the tourniquet cuff, for reading the usage limit record indicative of the predetermined limit and for calculating a second amount of cuff usage while the cuff is connected to the tourniquet instrument, wherein the tourniquet instrument is operable to produce a usage alert signal if the second amount exceeds the predetermined limit.

10. The apparatus as described in claim 1 wherein the cuff is formed of materials having physical properties that are substantially unchanged at an elevated temperature sufficient to sterilize the cuff by autoclaving.

11. A tourniquet cuff apparatus, comprising
an inflatable portion having a length sufficient for encircling a patient's limb at a desired location;
a stiffener member inside the inflatable portion and including an aperture formed through the stiffener member;
a wireless cuff usage register attached to and contacting the stiffener member inside the inflatable portion and having an aperture formed therethrough that is concentric with the aperture in the attached stiffener member;
a tubular cuff connector extending through the concentric apertures in the stiffener member and usage register to communicate pneumatically with the interior of the inflatable portion, the connector further adapted for connecting to a tourniquet instrument to establish a releasable pneumatic connection therewith.

12. The cuff apparatus of claim 11 wherein the wireless cuff usage register is adhesively bonded to the stiffener member.

* * * * *